United States Patent
Karrowni et al.

(10) Patent No.: US 12,011,173 B2
(45) Date of Patent: Jun. 18, 2024

(54) DUAL BALLOON CATHETER AND RELATED METHODS FOR TREATMENT OF HEART FAILURE

(71) Applicant: Kar Health, LLC, Iowa City, IA (US)

(72) Inventors: Wassef Karrowni, Cedar Rapids, IA (US); Mirna Karouni, Cedar Rapids, IA (US)

(73) Assignee: Kar Health, LLC, Irvine, CA (US)

( * ) Notice: Subject to any disclaimer, the term of this patent is extended or adjusted under 35 U.S.C. 154(b) by 234 days.

(21) Appl. No.: 17/566,075

(22) Filed: Dec. 30, 2021

(65) Prior Publication Data

US 2022/0202423 A1 Jun. 30, 2022

Related U.S. Application Data

(60) Provisional application No. 63/131,956, filed on Dec. 30, 2020.

(51) Int. Cl.
*A61B 17/12* (2006.01)

(52) U.S. Cl.
CPC .. *A61B 17/12045* (2013.01); *A61B 17/12109* (2013.01); *A61B 17/12136* (2013.01)

(58) Field of Classification Search
CPC ........ A61B 17/12045; A61B 17/12109; A61B 17/12136; A61M 25/10; A61M 25/1011; A61M 2025/1043; A61M 2025/1052
See application file for complete search history.

(56) References Cited

U.S. PATENT DOCUMENTS

| | | | |
|---|---|---|---|
| 4,546,759 A | 10/1985 | Solar | |
| 6,699,231 B1 * | 3/2004 | Sterman | A61M 1/3613 604/93.01 |
| 6,848,448 B1 * | 2/2005 | St. Germain | A61B 17/12136 128/898 |
| 7,849,861 B2 | 12/2010 | Ravikumar | |
| 8,968,239 B2 * | 3/2015 | Herrera | A61B 17/12136 604/103.08 |
| 9,393,384 B1 | 7/2016 | Kapur et al. | |
| 11,013,515 B2 * | 5/2021 | Zhadkevich | A61B 17/12031 |
| 11,230,649 B2 | 1/2022 | Mihara et al. | |
| 11,426,563 B2 * | 8/2022 | Rowe | A61M 60/33 |
| 11,464,892 B2 * | 10/2022 | Lane | A61M 1/3613 |
| 2009/0275889 A1 * | 11/2009 | Ravikumar | A61M 25/1011 604/101.05 |
| 2010/0331876 A1 | 12/2010 | Cadeno | |
| 2018/0346767 A1 * | 12/2018 | Mihara | C09J 11/06 |
| 2019/0167271 A1 * | 6/2019 | Zhadkevich | A61M 25/09 |
| 2020/0038575 A1 * | 2/2020 | Lane | A61M 1/3639 |
| 2021/0177425 A1 | 6/2021 | Kapur et al. | |

(Continued)

FOREIGN PATENT DOCUMENTS

WO 2020117844 A1 6/2020

*Primary Examiner* — Ryan J. Severson
(74) *Attorney, Agent, or Firm* — Dentons Davis Brown, P.C.; Kassandra Ricklefs

(57) ABSTRACT

A dual balloon catheter having two independently inflatable balloons that provides complete or intermittent synchronous occlusion of blood vessels (such as the contralateral iliac veins, for example) via the balloons, which can be used for the purpose of decreasing the pressure in the inferior vena cava, which results in decongestion of the kidneys, liver/splanchnic compartment, lymphatic system, and the heart.

9 Claims, 3 Drawing Sheets

(56) References Cited

U.S. PATENT DOCUMENTS

| | | | |
|---|---|---|---|
| 2022/0001154 A1* | 1/2022 | Rowe | A61M 25/1011 |
| 2022/0202423 A1* | 6/2022 | Karrowni | A61M 60/31 |
| 2022/0355085 A1* | 11/2022 | Rowe | A61M 60/841 |
| 2023/0389935 A1* | 12/2023 | Korkuch | A61B 17/12136 |

* cited by examiner

DUAL BALLOON CATHETER AND RELATED METHODS FOR TREATMENT OF HEART FAILURE

CROSS-REFERENCE TO RELATED APPLICATIONS

This application claims priority to U.S. Provisional Patent Application No. 63/131,956, filed Dec. 30, 2020 and entitled "Dual Balloon Catheter and Related Methods for Treatment of Heart Failure," which is hereby incorporated by reference in its entirety.

FIELD

The various embodiments herein relate to catheter technologies, especially as they relate to treatments for congestive heart failure.

BACKGROUND

Congestive heart failure (CHF) is a common disease and is the dominant cause of morbidity, mortality, and health care expenditures in the United States. Congestion, secondary to elevated filling pressures in the heart chambers, is believed to be a predominant cause of symptoms and adverse events in CHF patients. The clinical consequences of congestion include pulmonary edema (fluids in the lungs), renal congestion, liver or hepatic congestion, splanchnic (abdominal) congestion, and edema in the lower extremities.

Worsening kidney function is common in acute decompensated CHF and is known as cardiorenal syndrome. In addition to low cardiac output, renal congestion is a predominant mechanism for worsening kidney function in these patients. Evolving evidence suggests that renal congestion is one of the most important prognostic factors in CHF patients and is associated with increased morbidity and mortality. Multiple physiologic mechanisms lead to or exacerbate renal congestion in CHF patients, including low cardiac output and the increase in central venous pressure (CVP) and inferior vena cava (IVC) pressure associated with CHF.

It has been shown that kidney function and abdominal congestion are linked. For example, renal congestion leads to a vicious cycle with subsequent worsening renal function, more fluids retention, and worsening CHF. These subsequently lead to liver and splanchnic congestion, and thus increase in intraabdominal pressure. Further, the increase in the intraabdominal pressure can lead to a greater increase in IVC pressure and more kidney congestion.

In addition, disrupted intravascular fluid distribution as a result of the interactions between the splanchnic vascular compartment with the kidneys might play a significant role in the process of CHF decompensation even in the absence of increases of total body salt and water.

Another link between kidney function and abdominal congestion is through local reflex systems such as stretch receptors (mechanoreceptors) in the venous wall of the hepatic (portal) and splenic systems. Other deleterious effects of congestion commonly seen in CHF is liver (hepatic) congestion which if left untreated could ultimately lead to liver failure and cirrhosis.

In addition, the lymphatic system which collects fluid that has nourished the tissues and returns it to the veins via the thoracic and lymphatic ducts is also altered in CHF. The elevated venous pressure makes lymphatic drainage at these ducts deficient, thus causing secondary accumulation of fluids in the interstitial system and more congestion and worsening renal function.

There is a need in the art for an improved device and related methods for renal and splanchnic decongestion.

BRIEF SUMMARY

Discussed herein are various devices, systems and methods relating to catheter technologies, especially as they relate to treatments for congestive heart failure. Namely, the various Examples relate to a cardiac catheter having one or more balloons.

In Example 1, a balloon catheter comprising a catheter body, a first inflatable body disposed along a length of the catheter body, a first lumen defined in the catheter body, the first lumen in fluidic communication with the first inflatable body, a second inflatable body disposed along a length of the catheter body and distal of the first inflatable body, a second lumen defined in the catheter body, the second lumen in fluidic communication with the second inflatable body, and a controller operably coupled to the first and second inflatable bodies, wherein the controller is configured to separately inflate the first and second inflatable bodies according to an inflation schedule.

In Example 2, the balloon catheter of Example 1, wherein the inflation schedule comprises concurrent inflation, alternating inflation, or overlapping inflation of the first and second inflatable bodies.

In Example 3, the balloon catheter of Example 1, wherein the second inflatable body is disposed at a distance from the first inflatable body along the catheter body sufficient to allow for positioning the first inflatable body in a first predetermined blood vessel and the second inflatable body in a second predetermined blood vessel.

In Example 4, the balloon catheter of Example 3, wherein the first blood vessel is a first iliac vein and the second blood vessel is a second, contralateral iliac vein.

In Example 5, the balloon catheter of Example 1, further comprising a guidewire lumen defined through a length of the catheter body.

In Example 6, the balloon catheter of Example 1, further comprising a pressure sensor associated with the catheter body.

In Example 7, the balloon catheter of Example 6, wherein the pressure sensor comprises a pressure monitoring opening defined in the catheter body between the first and second inflatable bodies.

In Example 8, the balloon catheter of Example 6, wherein the controller is configured to adjust the inflation schedule based on pressure information collected by the pressure sensor.

In Example 9, a method of renal decongestion, the method comprising positioning a balloon catheter into a patient such that a first inflatable body of the balloon catheter is disposed in a right iliac vein and a second inflatable body of the balloon catheter is disposed in a left iliac vein, and inflating the first and second inflatable bodies according to an inflation schedule to reduce blood flow in the right and left iliac veins such that pressure in the inferior vena cava is decreased.

In Example 10, the method of Example 9, wherein the inflating the first and second inflatable bodies according to the inflation schedule comprises alternatingly inflating the first and second inflatable bodies.

In Example 11, the method of Example 9, wherein the inflating the first and second inflatable bodies according to the inflation schedule comprises concurrently inflating the first and second inflatable bodies.

In Example 12, the method of Example 9, wherein the inflating the first and second inflatable bodies according to the inflation schedule comprises periods of alternatingly inflating the first and second inflatable bodies and periods of concurrently inflating the first and second inflatable bodies.

In Example 13, the method of Example 9, further comprising modifying the inflation schedule based on a pressure level detected in the interior vena cava.

In Example 14, the method of Example 9, wherein the positioning the balloon catheter further comprises advancing the balloon catheter over a guidewire.

In Example 15, the method of Example 9, wherein the decrease in the pressure in the inferior vena cava subsequently results in pressure in renal veins being decreased.

In Example 16, a method of liver/splanchnic decongestion, the method comprising positioning a balloon catheter into a patient such that a first inflatable body of the balloon catheter is disposed in a right iliac vein and a second inflatable body of the balloon catheter is disposed in a left iliac vein, and inflating the first and second inflatable bodies according to an inflation schedule to reduce blood flow in the right and left iliac veins such that pressure in the inferior vena cava and subsequently the pressure in the hepatic veins and splanchnic veins are decreased.

In Example 17, a method of heart decongestion, the method comprising positioning a balloon catheter into a patient such that a first inflatable body of the balloon catheter is disposed in a right iliac vein and a second inflatable body of the balloon catheter is disposed in a left iliac vein, and inflating the first and second inflatable bodies according to an inflation schedule to reduce blood flow in the right and left iliac veins such that pressure in the inferior vena cava and subsequently the pressure in the right sided heart chambers are decreased.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

The various device embodiments disclosed or contemplated herein relate to a catheter having two inflatable balloons disposed thereon. In accordance with certain implementations, the various device embodiments can provide central venous decongestion by a method of using the device that provides immediate decrease in IVC pressure and CVP, and which offloads the renals, hepatic/splanchnic system, the lymphatic system, and the heart, thereby improving their physiologic efficiency and breaking the vicious cycle between congestion and worsening function of the organs. Further, in some embodiments, the use of the device and methods as disclosed or contemplated herein can accomplish these effects without the need to induce decompensations in the cardiac output and/or blood pressure and also without worsening of renal function.

Without being limited by theory, it is believed that CHF therapies should include decongestion of the cardiovascular system with focus not only on the heart filling pressure (preload) but also on congestion of at least the renal system, and, in some additional embodiments, also on congestion of the hepatic/splanchnic system and lymphatic drainage. Current therapeutic interventions focus solely on decreasing congestion of the cardiovascular system and include medications (diuretics, vasodilators, natriuretic peptides, V2R antagonists, etc), intravascular fluid removal with ultrafiltration or dialysis, and left ventricular assist devices. In contrast, the various device and method embodiments disclosed or contemplated herein combine control of congestion with simultaneous improvement/preservation of renal function.

Figure 1:
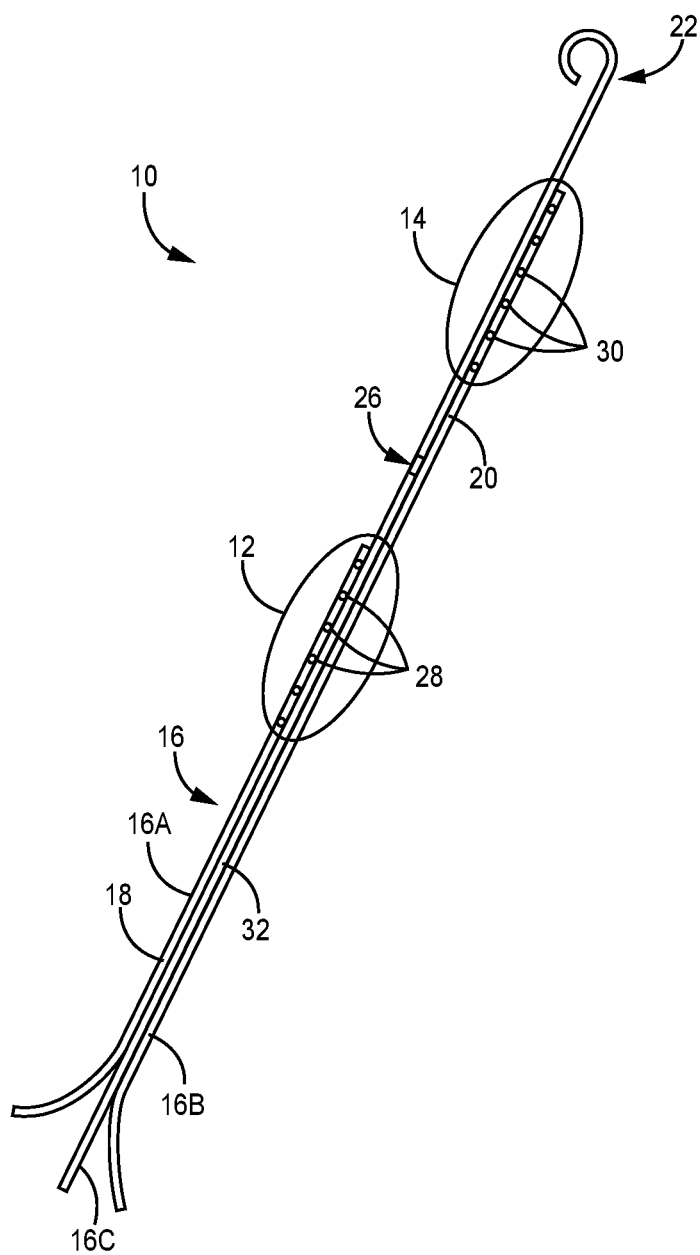
FIG. 1 is a top, perspective view of an exemplary embodiment of the catheter, according to one implementation.

One exemplary embodiment of a catheter 10 with two inflatable balloons 12, 14 is depicted in FIG. 1. The catheter 10 has a body 16 with three lumens: a first lumen 18 in fluidic communication with the first balloon 12, a second lumen 20 in fluidic communication with the second balloon 14, and a third lumen 32 through which a guidewire can be positioned and/or with which a pressure sensor (such as the sensor 26 discussed in detail below) can be associated. In one embodiment, the second balloon 14 is disposed at the distal end of the catheter body 16. Alternatively, in the exemplary implementation as shown, the second balloon 14 is disposed at some distance proximal from the distal end 22 of the catheter body 16.

The catheter body 16 is a flexible body that allows for easy insertion into and positioning within a target blood vessel such that the two balloons 12, 14 are positioned as desired, as described in additional detail below. In one embodiment, the body 16 is a single, unitary component 16 having three lumens 18, 20, 32 defined therein. Alternatively, in the exemplary implementation depicted in FIG. 1, the body 16 is made up of three separate tubular bodies 16A, 16B, 16C that are attached or otherwise secured together to make up the body 16. More specifically, the first tubular body 16A has the first lumen 18 defined therein, the second tubular body 16B has the second lumen 20 defined therein, and the third tubular body 16C is attached to both of the first and second tubular bodies 16A, 16B, has the third lumen 32 defined therein, and extends distally beyond the second balloon 14 such that the distal end of the third tubular body 16C is the distal end 22 of the body 16. Alternatively, the catheter body 16 can have two, four, or any number of lumens. In a further alternative, the catheter body 16 can take any known form or configuration.

The catheter body 16 can be made of stainless steel, Platinum, or nitinol. Alternatively, it can be made of polyester, nylon, silicone, or Teflon. In a further alternative, the body 16 can be made of any known material for use in intravenous catheters. Each of the catheter lumens (such as lumens 18, 20, 32), in certain implementations, can have an inner lining or inner surface. According to some embodiments, the inner lining or surface can be made of polytetrafluoroethylene, fluorinated ethylene propylene, or similar materials that facilitate the passage of fluid, gas, or any known medical device, such as, for example, a guidewire. In further implementations, the catheter body 16 can have an external coating which, in certain embodiments, can be made of polyurethane, polyethylene or other known polymers or materials to provide flexibility and support to the catheter body 16. The balloons 12, 14 can be made of nylon, silicone, polyurethane, or any other known material. Further, the size (diameter and length) of each balloon 12, 14, can, according to certain embodiments, vary based on the physical dimensions of the individual patient. Alternatively, various versions of the device 10 can be provided with balloons 12, 14 of varying, predetermined sizes.

Figure 2A:
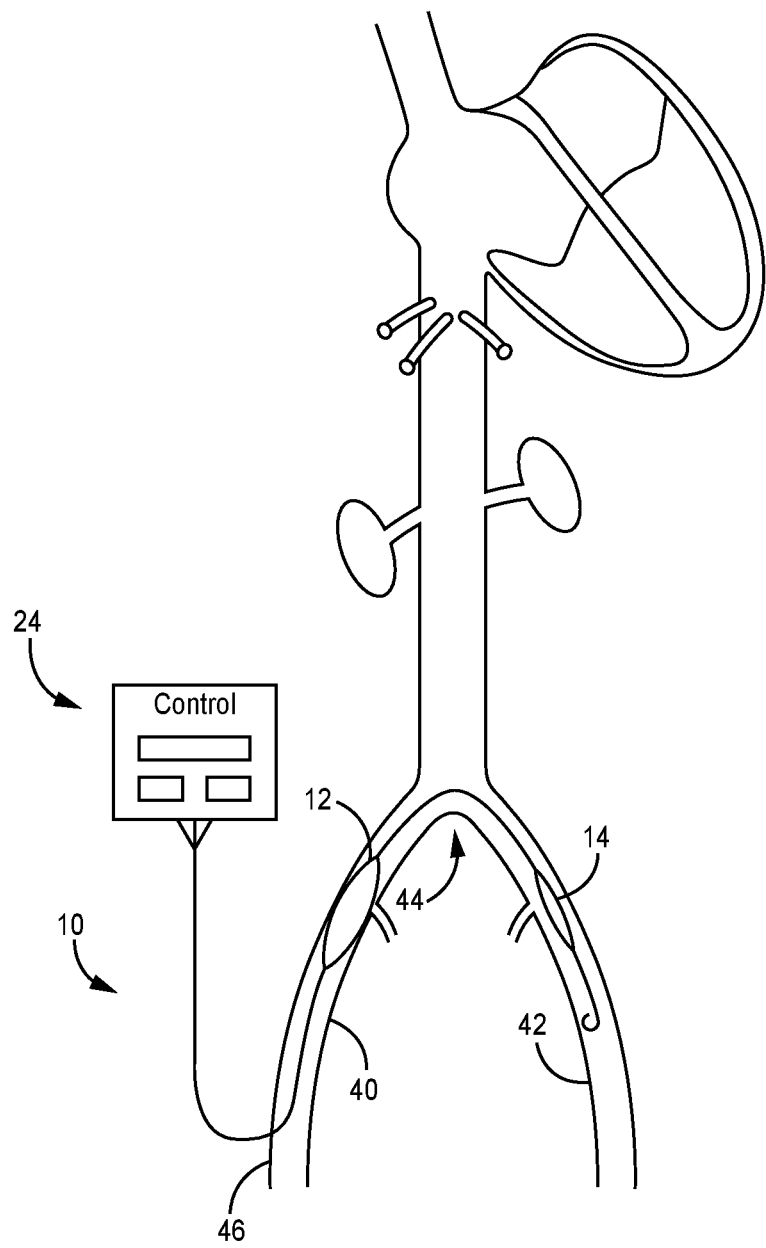
FIG. 2A is a schematic view of the catheter having two balloons inserted into the body, according to one implementation.
Figure 2B:
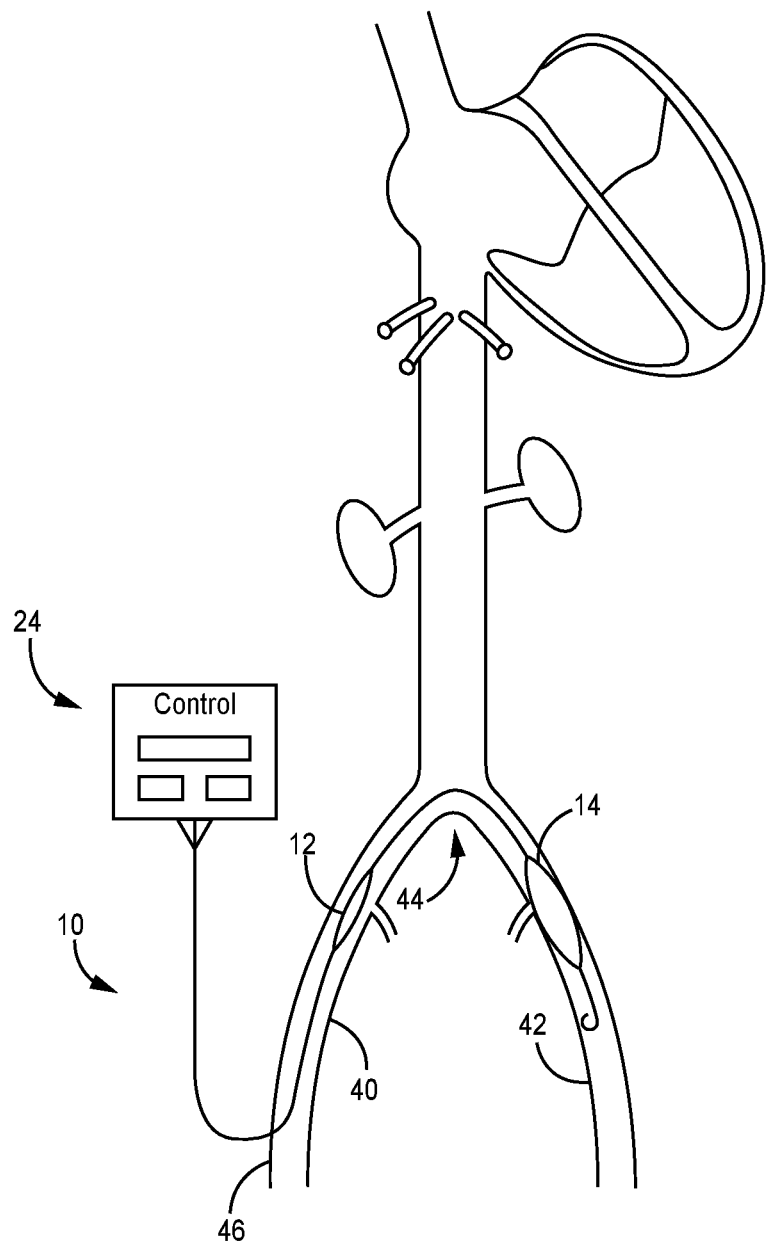
FIG. 2B is a further schematic view of the catheter having two balloons inserted into the body, according to one implementation.

As mentioned above, the first lumen 18 is in fluidic communication with the interior of the first balloon 12, and the second lumen 20 is in fluidic communication with the interior of the second balloon 14. More specifically, according to one embodiment, first balloon openings 28 are defined in the length of the body 16 that is disposed within the first balloon 12 and are in fluidic communication with the first lumen 18 such that the lumen 18 is in fluidic communication with the interior of the first balloon 12. Similarly, second balloon openings 30 are defined in the length of the body 16 that is disposed within the second balloon 14 and are in fluidic communication with the second lumen 20 such that the lumen 20 is in fluidic communication with the interior of the second balloon 14. Further, both lumens 18, 20 extend proximally along the catheter body 16 to a controller 24 to which the body 16 is coupled and which is disposed at a location that is external to the patient and in the procedural environment, as best shown in FIGS. 2A and 2B. Thus, the catheter body 16 is coupled at its proximal end to the controller 24 such that the first and second lumens 18, 20 are both in fluidic communication with an inflation/deflation mechanism (not shown) or two separate such mechanisms that separately control the fluidic pressure in the first and second lumens 18, 20 such that the mechanism(s) thereby control the inflation and deflation of the first and second balloons 12, 14, respectively.

The fluid that is disposed in the lumens 18, 20 and used to inflate the balloons 12, 14 can be a gas or a liquid. In one embodiment, the fluid is a gas that is helium, CO2, or the like. Alternatively, the inflation fluid can be any known fluid for use in an inflation balloon in a medical device.

In one embodiment, the length of the catheter body 16 and the distance between the two balloons 12, 14 on the body 16 can be determined by the size of the patient. More specifically, in certain implementations, the catheter body 16 length and the distance between the balloons 12, 14 on the body can be predetermined dimensions that ensure proper placement of the catheter body 16 in the target blood vessel(s) (such as, for example, the two contralateral common/external iliac veins) and proper positioning of the balloons 12, 14 therein, as will be described in further detail below.

In certain alternative implementations, the catheter body 16 can also have a pressure monitoring opening 26 defined in the body 16. In one embodiment, the opening 26 is defined in the body 16 along the length of the body 16 between the first and second balloons 12, 14. The opening 26 can be in fluidic communication with a third lumen 32 defined within the body 16. According to one embodiment, the opening 26 and lumen 32 can be used to monitor the pressure waveform from the IVC. According to certain implementations, the opening 26 and lumen 32 can be used to continuously monitor the pressure and further can be used as a feedback mechanism to control the inflation of the balloons 12, 14 and thereby impact the pressure, as will be described in additional detail below. Alternatively, the catheter body 16 can have any known pressure sensor or monitor for use in tracking the pressure in the IVC.

In accordance with some embodiments, the distal end 22 of the device body 16 can have a flexible curled (or "pigtail") shape as shown in FIG. 1. The curled shape can help to prevent vascular damage during movement of the device 10 into position and further can facilitate repositioning of the catheter 10. Alternatively, the distal end 22 can take any known shape or configuration.

The control system 24 is configured to regulate the inflation and deflation of the balloons 12, 14, as mentioned above. More specifically, according to certain implementations, the parameters controlled by the control system 24 can include any one or more of the following: (1) the volume of inflation/deflation fluid in each balloon 12, 14; (2) the rate (volume/time) at which the inflation/deflation fluid is urged into and out of each balloon 12, 14; (3) the time period during which each balloon 12, 14 remains inflated; and (4) the timing of inflation and deflation of each balloon 12, 14, including in relation to each other, such that inflation and deflation of each balloon 12, 14 can be timed to, for example, alternate or be simultaneous with the other balloon 12, 14. Further, in certain implementations in which the catheter 10 has a pressure sensor (such as the sensor 26 discussed above), the control system 24 can also be configured to display information about the pressure level from the pressure sensor (such as sensor 26). According to some embodiments, the control system 24 can display continuous information based on the continuous monitoring of the pressure waveforms transmitted from the IVC via the lumen 32 as described above.

In use as best shown in FIGS. 2A and 2B, a catheter device 10 with two balloons 12, 14 (similar or identical to the device shown in FIG. 1) can be introduced into a blood vessel for use in occluding blood flow therein. In one specific exemplary embodiment, the device 10 can be introduced into the common femoral vein 46 and positioned such that the first balloon 12 is disposed in the right common/external iliac vein 40 and the second balloon 14 is disposed in the left common/external iliac vein 42. In one embodiment, the device 10 can be advanced into the desired position over a guidewire. More specifically, the device 10 can be advanced from one side of the iliac venous system to the other up and over the IVC bifurcation 44 over the guidewire. Alternatively, the device 10 can be positioned in the desired position via any known method.

In certain embodiments, the device 10 can be positioned in the desired location for a few hours. Alternatively, the device 10 can be positioned in the desired location within the patient for several days.

According to some implementations, the device 10 can be positioned or repositioned using external visual guidance. For example, fluoroscopy or ultrasound guidance can be used to ensure that the device 10 is positioned as desired. Alternatively, any known technology for positioning the device 10 can be used.

In certain embodiments or situations, one or both of the balloons 12, 14 can be fully inflated to completely occlude one or both of the veins 40, 42. Alternatively, one or both of the balloons 12, 14 can be partially inflated to partially occlude one or both of the veins 40, 42. In use, the alternating inflation of the balloons 12, 14 can provide alternating intermittent occlusion of either iliac vein 40, 42 to decrease the venous pressure in the inferior vena cava (IVC).

As mentioned above, certain implementations of the device 10 can have a pressure monitor 26 that allows for monitoring the pressure in the IVC. The monitor 26 is coupled to the external control system 24 such that the control system 24 can be used to track the IVC pressure. During use, the real-time information about the IVC pressure can be used to adjust the use of the device 10 and thereby achieve the desired IVC pressure.

The various methods of using the device embodiments disclosed or contemplated herein can provide immediate central venous decongestion in patients with acute congestive heart failure (CHF). For example, in certain embodiments, the device 10 is positioned as described above such that the first balloon 12 is disposed in the right common/external iliac vein 40 and the second balloon 14 is disposed in the left common/external iliac vein 42. In this position, the balloons 12, 14 can be inflated concurrently or intermittently or in any pattern as described above to reduce the blood flow from the iliac veins 40, 42 to the heart 50. For example, in one exemplary embodiment, the controller (such as control system 24) can inflate a first of the two balloons 12, 14 for a predetermined inflation period of time, and then deflate the first balloon while simultaneously inflating the second of the two balloons 12, 14 for a predetermined inflation period of time and then repeat that cycle for a predetermined treatment period such that at least one of the two balloons 12, 14 is inflated at all times during the treatment period. In one specific embodiment, the predetermined inflation periods can vary from about 1 to about 10 minutes. Alternatively, the inflation periods can vary from about 2 to about 8 minutes. In a further alternative, the inflation periods can vary from about 3 to about 5 minutes. According to yet another alternative, the inflation periods can be any period of time, the treatment period can be any period of time, and the inflation pattern can be any known pattern.

This reduction in blood flow to the heart 50 causes a reduction in the pressure in the inferior vena cava ("IVC"). The resulting decreased pressure in the IVC as a result of the devices/methods herein can result in an increase in the outflow (decongestion) from the kidneys, liver/splanchnic compartment, and lymphatics, and decrease the heart chambers filling pressure (preload). Offloading these organs can improve their physiologic functions, thereby breaking the vicious cycle between congestion and worsening organ function.

Further benefits can include, for example, any one or more of interruption of the hepatorenal/splenorenal and cardiorenal reflexes with subsequent improvement in renal function, improved diuresis, and an increase in the efficiency of kidney function by improving the glomerular filtration rate and increase the tubular excretion of sodium/water. In addition, the removal of fluids from the extravascular fluid compartment (for example the splanchnic compartment) lead to a decrease in the intrabdominal pressure, and/or improvement in abdominal and thoracic lymphatic drainage. These could be achieved without risking the decompensation from forceful removal of intravascular volume with subsequent vascular underfilling or hypotension, and an increase in the activation or the global output of the sympathetic nervous system which causes renal vasoconstriction and a state of neurohormonal activation which have deleterious effects on the cardiovascular system.

Another benefit relates to the alternating occlusion of the two iliac veins. While complete occlusion of the IVC can cause serious problems, the alternating occlusion provided by the various device and method embodiments herein provides smooth and continuous reduction in venous pressure and venous return. In contrast, rapid fluctuations in the venous pressure and venous return related to inflation or deflation of a balloon in the IVC or the SVC can lead to a significant decrease in cardiac output and blood pressure, worsening kidney function, and retention of sodium and water.

Further, the ability of the device and method embodiments herein to vary the degree and interval of the occlusion of both or either of the iliac veins results in a wider range of titration options depending on the physiologic response of the heart, kidneys, and hepatic/splanchnic organs.

Another advantage of the various device embodiments herein is that they are safe relative to other devices, because they are placed in the pelvic area, away from cardiac structures where trauma can be devastating. Further, the ease of placement of the device using standard techniques and the ease of confirmation of the correct positioning of the device using either X-ray, ultrasound, or a similar technology enhances safety as well. In addition, the placement of the device embodiments herein in the pelvic area of the patient also avoids the IVC, where some patients have IVC filters. Plus, while known devices and techniques are mostly directed to help the heart recover from injury by decreasing preload, the various devices and methods herein combine the decreasing of preload with more direct decongestion of the kidneys, liver/splanchnic compartment, and the lymphatic system, thereby providing a more effective treatment.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

Although the various embodiments have been described with reference to preferred implementations, persons skilled in the art will recognize that changes may be made in form and detail without departing from the spirit and scope thereof.

What is claimed is:

1. A method of renal decongestion, the method comprising:
    positioning a balloon catheter into a patient such that a first inflatable body of the balloon catheter is disposed in a right iliac vein and a second inflatable body of the balloon catheter is disposed in a left iliac vein; and
    inflating the first and second inflatable bodies according to an inflation schedule to reduce blood flow in the right and left iliac veins such that pressure in the inferior vena cava is decreased.

2. The method of claim 1, wherein the inflating the first and second inflatable bodies according to the inflation schedule comprises alternatingly inflating the first and second inflatable bodies.

3. The method of claim 1, wherein the inflating the first and second inflatable bodies according to the inflation schedule comprises concurrently inflating the first and second inflatable bodies.

4. The method of claim 1, wherein the inflating the first and second inflatable bodies according to the inflation schedule comprises periods of alternatingly inflating the first and second inflatable bodies and periods of concurrently inflating the first and second inflatable bodies.

5. The method of claim 1, further comprising modifying the inflation schedule based on a pressure level detected in the interior vena cava.

6. The method of claim 1, wherein the positioning the balloon catheter further comprises advancing the balloon catheter over a guidewire.

7. The method of claim 1, wherein the decrease in the pressure in the inferior vena cava subsequently results in pressure in renal veins being decreased.

8. A method of liver/splanchnic decongestion, the method comprising:
   positioning a balloon catheter into a patient such that a first inflatable body of the balloon catheter is disposed in a right iliac vein and a second inflatable body of the balloon catheter is disposed in a left iliac vein; and
   inflating the first and second inflatable bodies according to an inflation schedule to reduce blood flow in the right and left iliac veins such that pressure in the inferior vena cava and subsequently the pressure in the hepatic veins and splanchnic veins are decreased.

9. A method of heart decongestion, the method comprising:
   positioning a balloon catheter into a patient such that a first inflatable body of the balloon catheter is disposed in a right iliac vein and a second inflatable body of the balloon catheter is disposed in a left iliac vein; and
   inflating the first and second inflatable bodies according to an inflation schedule to reduce blood flow in the right and left iliac veins such that pressure in the inferior vena cava and subsequently the pressure in the right sided heart chambers are decreased.

* * * * *